United States Patent [19]

Mendoza

[11] Patent Number: 4,588,816

[45] Date of Patent: May 13, 1986

[54] PREPARATION OF (2-(6-SUBSTITUTED)-PYRIDINYLOXY)ALKANOLS FROM 2-(6-SUBSTITUTED)PYRIDINOLS AND ORGANIC CARBONATES

[75] Inventor: Abel Mendoza, Midland, Mich.

[73] Assignee: The Dow Chemical Company, Midland, Mich.

[21] Appl. No.: 608,069

[22] Filed: May 8, 1984

Related U.S. Application Data

[63] Continuation-in-part of Ser. No. 420,173, Sep. 20, 1982, abandoned.

[51] Int. Cl.$^4$ .............................................. C07D 213/64
[52] U.S. Cl. ................................. 546/301; 546/297; 546/298; 546/302
[58] Field of Search ................ 546/301, 302, 297, 298

[56] References Cited

PUBLICATIONS

Yoshino et al., J. C. S. Perkins I, p. 1266, (1977).
Newkome et al., J. Org. Chem., vol. 42, (9), p. 1500, (1977).
Newkome et al., J. Am. Chem. Soc., vol. 97, (11), pp. 3232-3234, (1975).

Primary Examiner—Alan L. Rotman

[57] ABSTRACT

The invention is a process for the preparation of (2-(6-substituted)pyridinyloxy)alkanols comprising contacting a 2-(6-substituted)pyridinol with an organic carbonate at a temperature of between about 0° C. and 250° C.

14 Claims, No Drawings

PREPARATION OF (2-(6-SUBSTITUTED)-PYRIDINYLOXY)ALKANOLS FROM 2-(6-SUBSTITUTED)PYRIDINOLS AND ORGANIC CARBONATES

CROSS-REFERENCE TO RELATED APPLICATION

This is a continuation-in-part of copending application Ser. No. 420,173 (incorporated herein by reference), filed Sept. 20, 1982 now abandoned.

BACKGROUND OF THE INVENTION

This invention relates to the preparation of (2-(6-substituted)pyridinyloxy)alkanols from 2-(6-substituted)-pyridinols and organic carbonates.

Newkome et al., "Chemistry of Heterocyclic Compounds. 23. Synthesis of Multiheteromacrocycles Posessing 2,6-Pyridino Subunits Connected by Carbon Oxygen Linkages", *J. Org. Chem.*, 42(9), 1500 (1977), teach that 2-(2-pyridinyloxy)ethanol can be prepared by reacting a 2-bromopyridine with a dianion of ethylene glycol, which was generated from sodium hydride and ethylene glycol.

Yoshino et al., "Synthetic Studies with Carbonates", *J. C. S. Perkins I*, 1266 (1977), teach that the reaction of a 2-pyridinol with an ethylene carbonate affords only 1-(2-hydroxyethyl)-2-pyridone. Yields of up to 75 percent of the 1-(2-hydroxyethyl)-2-pyridone are reported.

A novel process for preparing (2-(6-substituted)-pyridinyloxy)alkanols in high yields has been discovered.

SUMMARY OF THE INVENTION

The invention is a process for the preparation of (2-(6-substituted)pyridinyloxy)alkanols comprising contacting a 2-(6-substituted)pyridinol with an organic carbonate at a temperature of between about 0° C. and 250° C.

The process may further include contacting the 2-(6-substituted)pyridinol and the organic carbonate with a catalytic amount of a catalyst. The process may further include contacting the 2-(6-substituted)pyridinol and the organic carbonate in a suitable solvent.

The compounds prepared by this process are useful in preparing plastics, pharmaceuticals, agricultural chemicals and pyridine macrocyclic ethers.

DETAILED DESCRIPTION OF THE INVENTION

Preferred 2-(6-substituted)pyridinols include those represented by the formula:

$$\underset{R_1}{\overset{R_2}{\diagup}}\underset{N}{\overset{R_3}{\diagdown}}\underset{OH}{\overset{R_4}{\diagup}} \quad (I)$$

wherein:
$R_1$ is a halogen, alkyl, phenyl, haloalkyl, halobenzyl, halophenyl, or aryl-substituted alkyl;
$R_2$ is a halogen, hydrogen, alkyl, phenyl, carboxyl or aryl-substituted alkyl;
$R_3$ is a halogen, hydrogen, alkyl, phenyl or aryl-substituted alkyl; and
$R_4$ is a halogen, hydrogen, alkyl, phenyl, aryl-substituted alkyl, carboxyl, or a nitro group.

$R_1$ is more preferably a halogen, alkyl, benzyl, phenyl, haloalkyl, halobenzyl or halophenyl, even more preferably a halogen or $C_{1-12}$ alkyl, and most preferably a halogen or methyl. $R_2$, $R_3$ and $R_4$ are more preferably hydrogen, halogen or $C_{1-12}$ alkyl, and most preferably hydrogen or halogen.

The 2-(6-substituted)pyridinols and preparations thereof are known in the art, see Goodhue, U.S. Pat. No. 3,252,858; Zielinski, U.S. Pat. No. 3,535,328; Zielinski, U.S. Pat. No. 3,687,959; and H. Tuckelmann, "Pyridinols and Pyridones", *Pyridine and Its Derivatives, Part III*, Abramovich Ed., pp. 597–1181, Interscience, New York, N.Y. (1973) (all incorporated herein by reference).

2-(6-Substituted)pyridinol refers herein to any pyridinol which contains a substituent on the 6 position, that is, there is no hydrogen bonded to the 6 carbon.

Preferred organic carbonates are alkylene carbonates, cycloalkylene carbonates, and arylalkylene carbonates and may be represented by the formula:

$$\overset{O}{\underset{\underset{R_5}{CH}-\underset{R_5}{CH}}{\overset{\parallel}{O\diagdown C \diagup O}}} \quad (II)$$

wherein $R_5$ is independently in each occurrence hydrogen, $C_{1-5}$ alkyl, phenyl, aryl-substituted alkyl, glycidyl, hydroxy-substituted methyl, chloromethyl or each $R_5$ may be combined to form a $C_{3-10}$ alkylene group; in the latter case a cycloalkylene carbonate is formed. $R_5$ is more preferably hydrogen or $C_{1-5}$ alkyl, even more preferably hydrogen or methyl, and most preferably hydrogen. More preferable alkylene carbonates include ethylene carbonate, propylene carbonate and cyclohexylene carbonate, with ethylene carbonate being most preferred. The organic carbonates, and preparations thereof are well-known in the art, see Renga et al., U.S. Pat. No. 4,332,729; Renga et al., U.S. Pat. No. 4,331,604; DePasquale, U.S. Pat. No. 3,748,345; Emmons et al., U.S. Pat. No. 3,535,341; Lichtenwalter et al., U.S. Pat. No. 2,773,070; and Great Britain Patent application No. 2,011,402 (all incorporated herein by reference).

The (2-(6-substituted)pyridinyloxy)alkanols prepared by this process include those represented by the formula:

$$\underset{R_1}{\overset{R_2}{\diagup}}\underset{N}{\overset{R_3}{\diagdown}}\underset{\underset{R_5}{OCH}-\underset{R_5}{CHOH}}{\overset{R_4}{\diagup}} \quad (III)$$

wherein $R_1$, $R_2$, $R_3$, $R_4$ and $R_5$ are as defined above.

The process disclosed herein is illustrated by the following equation:

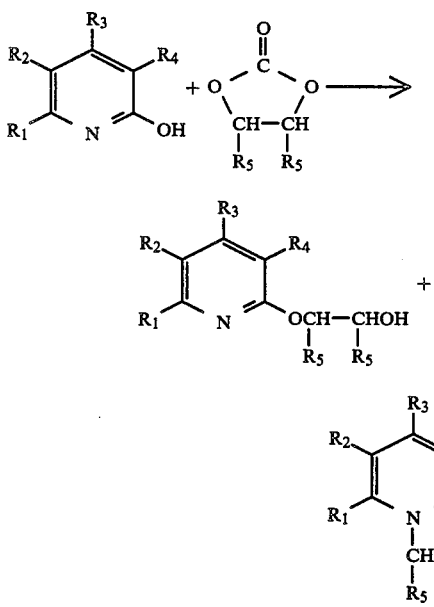

wherein $R_1$, $R_2$, $R_3$, $R_4$ and $R_5$ are as defined above.

This process generates 1-(2-hydroxyalkyl)-2-pyridones as by-products, which are the N-ethoxylated products. The relative ratio of the 2-(2-pyridinyloxy)alkanol, the O-ethoxylated product, to the 1-(2-hydroxyalkyl)-2-pyridone, the N-ethoxylated product, is influenced by whether there is a substituent on the 6 carbon. Where there is no substituent on the 6 carbon, the N-ethoxylated species is the prevalent product. Where there is a substituent on the 6 carbon, the O-ethoxylated species is the prevalent product. In the latter situation, the ratio of the O-ethoxylated species to N-ethoxylated species prepared can be as high as 4:1.

Surprisingly, wherein the 6 carbon has a substituent, the 2-(6-substituted-2-pyridinyloxy)ethanol is prepared in a 50 percent or greater yield. Under more preferred conditions, wherein the 6 carbon is substituted, the 2-(6-substituted-2-pyridinyloxy)ethanol is recovered in a 60 percent or greater yield, and under the most preferred conditions, in an 80 percent or greater yield.

This process can be run with or without a catalyst. When no catalyst is used, elevated temperatures are required for the reaction described to take place.

This reaction is catalyzed by bases. Preferred basic catalysts include tertiary amines, tetraalkyl phosphonium halides, tetraalkyl ammonium halides, alkali metal halides, alkali metal hydrides, alkali metal hydroxides, alkali metal carbonates, alkali metal stannates and alkali metal bicarbonates. More preferred catalysts include alkali metal halides, alkali metal carbontes and tetraalkyl phosphonium salts. The preferred alkali metals are sodium and potassium.

When a catalyst is used, at least that amount which catalyzes the reaction should be used. The upper limit on the amount of catalyst is dictated by economics. Preferably the amount of catalyst is between about 0.01 and 1.0 mole percent, and most preferably between about 0.02 and 0.2 mole percent.

Suitable reaction temperatures are between about 0° C. and 250° C. Preferably temperatures include between about 50° C. and 150° C. Below 50° C. the rate of reaction is slow when an economical amount of catalyst is used. 150° C. is about the boiling point of some of the suitable solvents which may be used in the process.

This process can be run with or without a solvent. A suitable solvent is either an excess of the organic carbonate reactant or a solvent which is inert to the reactants. Suitable inert solvents include aromatic hydrocarbons such as, toluene, benzene, ethylbenzene, xylene, and the like; ketones; ethers; dimethyl formamide; or tetrahydrofuran.

The organic carbonate and 2-(6-substituted)-pyridinol react in stoichiometric ratios. Where the organic carbonate is not used as a solvent, the organic carbonate and 2-(6-substituted)pyridinols are preferably reacted in a mole ratio of between about 1.2 to 1.0 and 1.0 to 1.0, respectively, most preferably between about 1.1 to 1.0 to 1.0 to 1.0.

The pressure can be atmospheric, superatmospheric or subatmospheric. Atmospheric pressure is preferred.

Reaction time affects the yields of the product. The reaction time is in turn affected by the amount of catalyst and the temperature used. As the amount of catalyst used and the reaction temperature decreases, the reaction time required for a reasonable yield of product increases. A reasonable lower limit on reaction time is about five minutes. The upper limit on reaction time is dictated by the economics of the process.

The products can be recovered by known methods such as distillation.

SPECIFIC EMBODIMENTS

The following examples are included for illustrative purposes only and do not limit the scope of the invention or the scope of the claims. All parts and percentages are by weight unless otherwise specified.

EXAMPLE 1

An 8.80-g portion of 6-methyl-2-pyridinol was added to 7.8 g of ethylene carbonate in 100 ml of dimethyl formamide, followed by 1.10 g of potassium carbonate. The resulting suspension was heated to 150° C. for 0.5 hour. Gas chromatographic analysis showed essentially complete reaction of the 6-methyl-2-pyridinol with products of 2-(6-methyl-2-pyridinyloxy)ethanol and 1-(2-hydroxyethyl)-6-methyl-2-pyridone in about a 4:1 ratio. Filtration of the catalyst, followed by removal of the solvent and distillation afforded a 60 percent yield of 2-(6-methyl-2-pyridinyloxy)ethanol.

EXAMPLE 2

A reaction similar to the one in Example 1 was run except no catalyst was used. After 4 hours at 150° C., 98 percent of the 6-methyl-2-pyridinol was reacted with a 4:1 ratio of 2-(6-methyl-2-pyridinyloxy)ethanol and 1-(2-hydroxyethyl)-6-methyl-2-pyridone in the product. Vacuum distillation afforded recovery of a 50 percent yield of 2-(6-methyl-2-pyridinyloxy)ethanol.

EXAMPLE 3

A solution of 6-methyl-2-pyridinol (4.40 g) and ethylene carbonate (4.20 g) in dimethyl formamide (50 ml) was heated with tetra-n-butyl phosphonium bromide (0.27 g) at 150° C. for 2 hours. 99 Percent of the 6-methyl-2-pyridinol reacted. The ratio of 2-(6-methyl-2-pyridinyloxy)ethanol to 1-(2-hydroxyethyl)-6-methyl-2-pyridone prepared was 4:1.

EXAMPLE 4-(not an example of this invention)

To a solution of 9.51 g of 2-pyridinol and 10.45 g of ethylene carbonate in 100 ml of dimethyl formamide was added potassium carbonate. The suspension was heated at 90° C. for 0.5 hour. Analysis of the reaction product by gas chromatography indicated the formation of 2-(2-pyridinyloxy)ethanol and 1-(2-hydroxyethyl)-2-pyridone in a molar ratio of 1:3. Filtration of the catalyst followed by removal of the solvent and distillation resulted in recovery of a 20 percent yield of 2-(2-pyridinyloxy)ethanol.

EXAMPLE 5

A solution of 15.6 g of 6-chloro-2-pyridinol and 11.7 g of ethylene carbonate in 125 ml of dimethyl formamide is heated at 150° C. for 1 hour in the presence of 1.65 g of potassium carbonate. Gas chromatographic analysis of the solution shows an essentially complete reaction of the 6-chloro-2-pyridinol with products 2-(6-chloro-2-pyridinyloxy)ethanol and 1-(2-hydroxyethyl)-6-chloro-2-pyridone in a 9:1 ratio. Filtration of the catalyst, followed by removal of the solvent and distillation under vacuum affords a 77 percent yield of a product identified by spectroscopic means as 2-(6-chloro-2-pyridinyloxy)ethanol.

What is claimed is:

1. A process for the preparation of (2-(6-substituted)-pyridinyloxy)alkanols comprising contacting a 2-(6-substituted)pyridinol with an organic carbonate at a temperature of between about 0° C. and 250° C., under conditions such that the (2-(6-substituted)pyridinyloxy)alkanols are prepared in a 50 percent by weight yield or greater.

2. The process of claim 1 wherein the 2-(6-substituted)pyridinol can be represented by the formula:

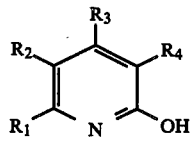
(I)

the (2-(6-substituted)pyridinyloxy)alkanols can be represented by the formula:

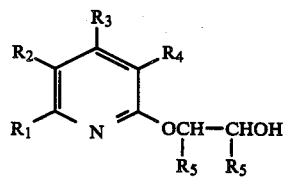
(III)

and the organic carbonates can be represented by the formula:

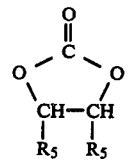
(II)

wherein:
$R_1$ is a halogen, alkyl, phenyl, haloalkyl, halobenzyl, halophenyl or aryl-substituted alkyl;
$R_2$ is a halogen, hydrogen, alkyl, phenyl, carboxyl or aryl-substituted alkyl;
$R_3$ is a halogen, hydrogen, alkyl, phenyl or aryl-substituted alkyl;
$R_4$ is a halogen, hydrogen, alkyl, phenyl, aryl-substituted alkyl, carboxyl, or a nitro group; and
$R_5$ is independently in each occurrence a hydrogen, $C_{1-5}$ alkyl, phenyl, aryl-substituted alkyl, chloromethyl or each $R_5$ may be combined to form a $C_{3-6}$ alkylene group.

3. The process of claim 2 wherein $R_1$ is a halogen, alkyl, phenyl, haloalkyl, halobenzyl or halophenyl.

4. The process of claim 3 wherein $R_1$ is a halogen or $C_{1-12}$ alkyl; and $R_2$, $R_3$ and $R_4$ are hydrogen, halogen or $C_{1-12}$ alkyl.

5. The process of claim 4 wherein $R_1$ is a halogen or methyl, and $R_2$, $R_3$ and $R_4$ are hydrogen or a halogen.

6. The process of claim 5 wherein $R_5$ is independently in each occurrence hydrogen, $C_{1-5}$ alkyl or each $R_5$ combines to form a $C_{3-10}$ alkylene group.

7. The process of claim 6 wherein the organic carbonate is ethylene carbonate, propylene carbonate or cyclohexylene carbonate.

8. The process of claim 1 which further includes contacting with the 2-(6-substituted)pyridinol and the organic carbonate, a catalytic amount of a catalyst wherein the catalyst is a tertiary amine, tetraalkyl ammonium halide, tetraalkyl phosphonium halide, alkali metal halide, alkali metal hydride, alkali metal hydroxide, alkali metal carbonate, alkali metal stannate or alkali metal bicarbonate.

9. The process of claim 8 wherein the catalyst is an alkali metal halide, alkali metal carbonate, or a tetraalkyl phosphonium halide.

10. The process of claim 9 wherein the alkali metal is sodium or potassium.

11. The process of claim 8 wherein the amount of the catalyst is between about 0.01 and 1.0 mole percent.

12. The process of claim 8 which further includes contacting the 2-(6-substituted)pyridinol and the organic carbonate in solvent.

13. The process of claim 12 wherein the solvent is an aromatic hydrocarbon, a ketone, an ether, dimethyl formamide, or tetrahydrofuran.

14. The process of claim 1, wherein the temperature is between about 50° C. and 150° C.

* * * * *